United States Patent [19]

Klein

[11] Patent Number: 5,302,272

[45] Date of Patent: Apr. 12, 1994

[54] FIBER OPTIC FLOW CELL FOR DETECTION OF ELECTROPHORESIS SEPARATION WITH A CAPILLARY COLUMN AND METHOD OF MAKING SAME

[75] Inventor: Gerald L. Klein, Orange, Calif.

[73] Assignee: Beckman Instruments, Inc., Fullerton, Calif.

[21] Appl. No.: 847,783

[22] Filed: Mar. 5, 1992

[51] Int. Cl.$^5$ .................... G01N 27/26; G01N 27/447
[52] U.S. Cl. ............................ 204/299 R; 204/180.1; 356/344
[58] Field of Search ............ 204/299 R, 180.1; 356/344, 436, 440, 432; 73/61.58; 250/373, 376

[56] References Cited

U.S. PATENT DOCUMENTS

| | | | |
|---|---|---|---|
| 4,675,300 | 6/1987 | Zare et al. | 356/344 X |
| 4,816,123 | 3/1989 | Ogan et al. | 204/183.3 |
| 5,110,431 | 5/1992 | Moring | 204/299 R X |

OTHER PUBLICATIONS

Frantisek Foret et al "On-Line Fiber Optic UV Detection Cell and Conductivity Cell for Capillary Zone Electrophoresis" Electrophoresis 7 (*1986) 430-432.
Takeshi Hirokawa et al "The Separation Process in Isotachophoresis I. A 32-Channel Ultraviolet-Photometric Zone Detector" Journal of Chromatography 463 (*1989) 39-49. *(No Month Available).

*Primary Examiner*—John Niebling
*Assistant Examiner*—John S. Starsiak, Jr.
*Attorney, Agent, or Firm*—William H. May; Gary T. Hampson; Charles Berman

[57] ABSTRACT

A capillary electrophoresis detector assembly including a separation column in which the components of a mixed sample are separated; an exit column which completes the connection to the terminal buffer reservoir; and a support sleeve which includes precisely positioned radial bores therethrough to allow insertion of optical fibers in the form of an input fiber which transmits the incoming radiation from an illumination source and an exit fiber which receives the radiation and relays same to a detector.

In fabricating the assembly, a precision wire is partially inserted into the output end of the separation column. The column/wire combination is inserted into one end of the sleeve. The exit column is threaded onto the precision wire and also inserted into the opposite end of the sleeve. The input and exit fibers are inserted into the radial bores in the sleeve until they touch the precision wire in opposition. Thus, the precision wire serves to establish the spacing between the optical fibers (as determined by the diameter of the wire). This technique affords a known, reproducible, optical path distance between the ends of the fibers. The capillary columns are further slide into the sleeve until they touch the optical fibers. The assembly of the sleeve and fibers is then bonded together whereupon the precision wire is removed.

16 Claims, 1 Drawing Sheet

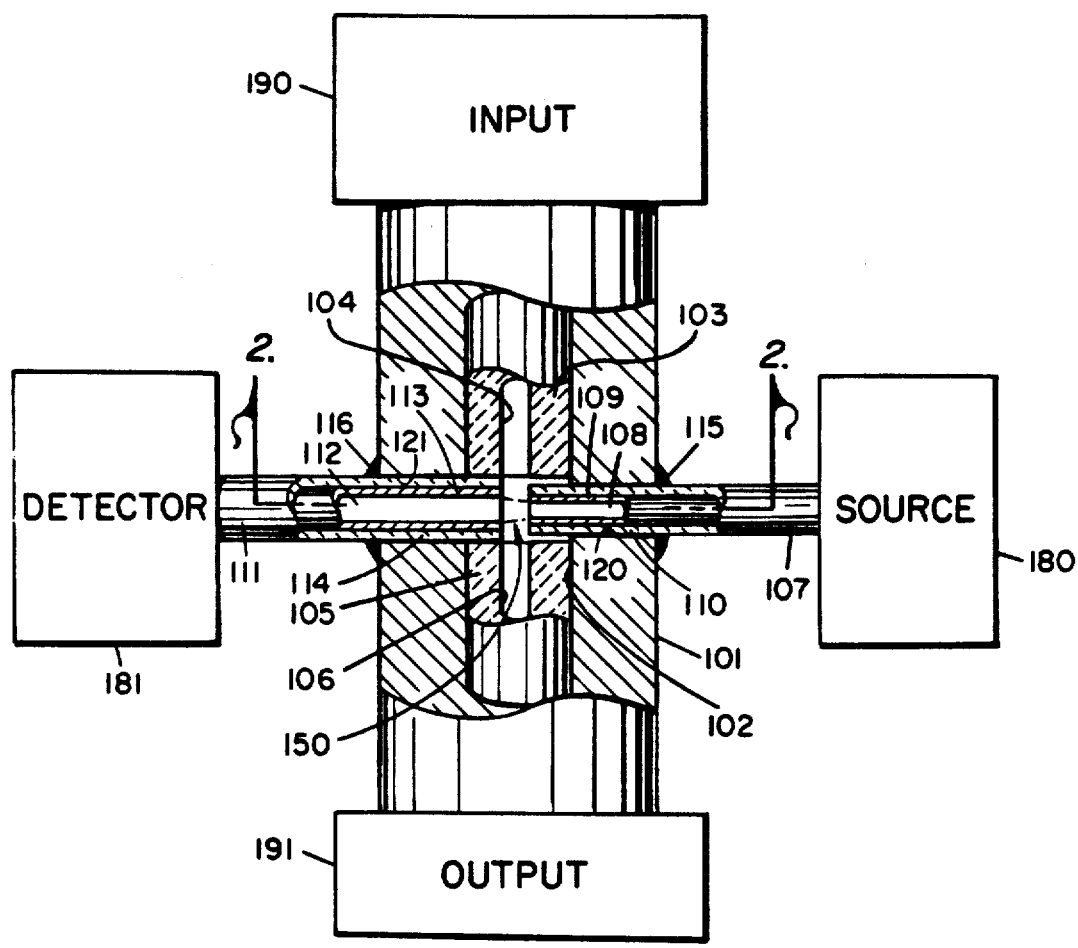
FIG. 1
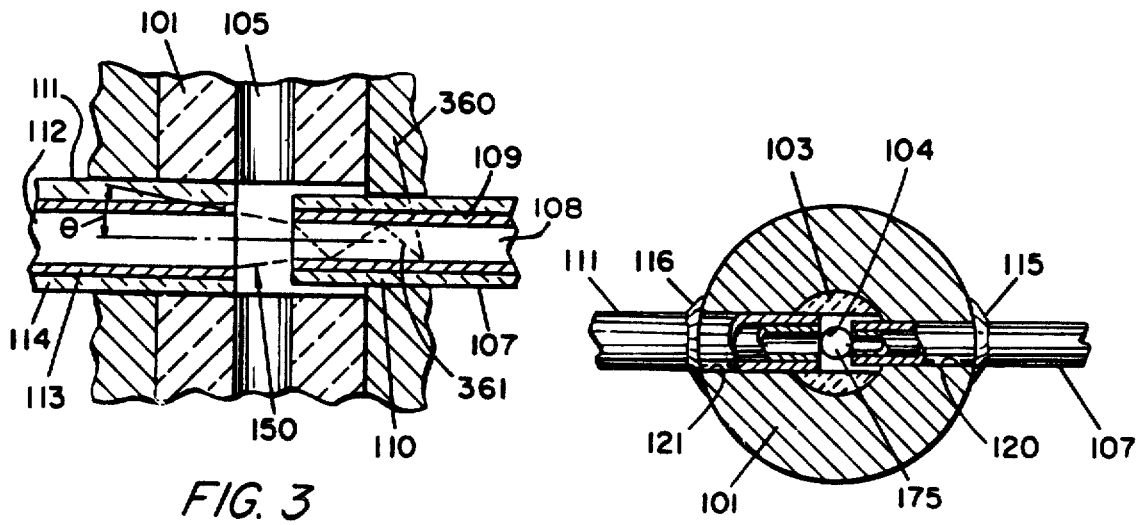
FIG. 3
FIG. 2

FIBER OPTIC FLOW CELL FOR DETECTION OF ELECTROPHORESIS SEPARATION WITH A CAPILLARY COLUMN AND METHOD OF MAKING SAME

BACKGROUND

1. Field of the Invention

This invention is directed to capillary electrophoresis detection, in general, and to precision detector assemblies using optical detection, in particular.

2. Prior Art

Capillary electrophoresis is an important emerging new technology. It offers significant advantages in separation of a wide range of compounds ranging from small ions to hole cells. The separation can be accomplished in several ways. The solution can be supplied to a medium of paper, gel starch or a liquid carrier buffer. The preferred method of interest herein is the latter method. That is, a solution is prepared which comprises a carrier buffer and a sample to be evaluated. This solution is stored in an input reservoir and, selectively, transported to an output reservoir. Typically, the solution is transported through a tube which is transparent (or at least translucent). The solution can be caused to be transported through the tube by applying a pressure or an electrical differential between the respective reservoirs. As the solution passes through the tube, it tends to separate. This is a well-known technique in the art.

One of the difficulties associated with the technology lies in the detection of the separated components as they migrate along the capillary column.

In the past, a technique reported by Tiselius (circa 1929) utilized an open U-tube filled with a buffer liquid and the sample. (This is sometimes referred to as the Schlieren technique.) In this arrangement, the separation of the sample components in the U-tube was visually observed. Obviously, this technique was extremely crude and provided relatively low accuracy results. For example, the tube was relatively large in diameter which did not cause the sample to separate to a fine degree. Also, the optics involved provided relatively gross observations and little detailed analysis.

Later (circa 1974), in a technique reported by Virtannen, separation of the samples in the observation tube was enhanced. This technique, referred to as isotachophoresis, improved the sample separation, but the optical observation apparatus was not significantly improved.

In or around 1980, Hjerten and Jorgenson developed the small bore tube (or capillary) technique for separation. This capillary approach was a significant development in electrophoresis technique. It provided several advantages including a minimizing effect of diffusion, a high number of theoretical plates and a smaller diameter observation field.

In this technique, light was directed across the capillary to enhance viewing of the sample. However, in this arrangement the light source and receiver were disposed outside the capillary tube. Moreover, the light source and receiver were, typically, disposed outside of a support sleeve in which the capillary was mounted. Thus, significant optical problems existed. For example, the perturbations and wall effects produced by the sleeve and/or capillary created some distortions and/or anomalies in the observed data. Because the sleeve and/or capillary presented cylindrical surfaces and because of the differences in indices of refraction, some of the incident light rays completely missed the sample. Likewise, some of the incident light rays traversed paths which were less than the entire sample. While these effects can be calculated to some degree and factored into the resultant data, this information is less than perfect and subject to question.

In 1987, Karger developed the gel column which has a significant sieving effect on the sample. However, the optics in this system are not significantly better than the other prior art devices.

The physical properties of the optics in such systems is important as the absorbance detection of samples is dependent upon the molar extinction (at a known wavelength) of the absorbing material, the concentration of the specimen and the path length through which the radiation must pass.

In other words, the equivalent absorbance A in this sample measuring technique is defined as $$A = kcl$$

where
 $k$ = the molar extinction coefficient;
 $c$ = concentration; and
 $l$ = path length through solution.

In a given analysis situation, the only component of this equation which can be effectively controlled is $l$. This factor is controlled by the optics of the apparatus. Thus, an improved optical arrangement is highly desirable in the electrophoresis measuring technology.

One of the problems in optical detection systems is stray light which, in general, may be described as any energy which reaches the detector without having been affected by the sample. Stray light can arise from either the direct optical path or from an external path.

The small size of the capillary column demands accuracy in placement of an optical detection system since most optical systems presently employed are located outside the capillary.

With the capillaries of vanishingly small dimensions (5-200 microns), extreme precision is required to assure that interrogating radiation passes through the bore of the capillary where the sample to be detected is located and, as well, to avoid any radiation "piping" around the bore through the capillary material or even passing by the capillary totally.

With optical fibers, there is an angle of acceptance which contains and propagates the light. A numerical aperture, which is the sine of half the angle of acceptance for the fiber, defines the angle of propagation through the fiber. Light entering the fiber at angles greater than this value leaks away and is not propagated to the output end.

The present invention provides an apparatus with the optical detection system inside the capillary column, thereby eliminating alignment difficulties, and other advantages disclosed herein.

SUMMARY OF THE INSTANT INVENTION

This invention comprises a capillary electrophoresis detection assembly. The assembly includes an input column in which the components of a mixed sample are separated and supplied to the detector site. An exit column is aligned with the input column and completes the connection to the output reservoir. A support sleeve with a bore therethrough receives at least portions of the input and exit columns. At least a pair of radial precision holes are drilled through the sleeve. Optical fibers in the form of an input fiber which transmits the incoming radiation and an exit fiber which picks up the radiation for relaying to the detector pass through the holes in the sleeve.

In fabricating the assembly, a precision wire is inserted part way into the end of one of the columns. The column with the wire extending therefrom is inserted into the sleeve with the wire passing out of the other end of the sleeve. The other column is slipped onto the precision wire and also inserted into the sleeve from the opposite end. Typically, the columns are not in contact. The input and exit optical fibers are inserted into the cross holes in the sleeve until they touch the precision wire in opposition. The precision wire serves to establish the precise, reproducible spacing between the optical fibers. The capillary columns are then slid further into the sleeve until they touch the optical fibers. The assembly is then bonded. The precision wire is removed.

BRIEF DESCRIPTION OF THE DRAWINGS

FIG. 1 is a partially sectioned view of a detector in accordance with the instant invention.

FIG. 2 is a cross-sectional view through the detector taken along the lines 2—2 in FIG. 1.

FIG. 3 is an enlarged cross-sectional view of the light envelope produced by the detector of the instant invention.

DESCRIPTION OF A PREFERRED EMBODIMENT

Referring now to FIG. 1, there is shown a partially cross-sectional view of a detector assembly 100 fabricated in accordance with the instant invention.

The detector assembly 100 includes an outer support sleeve 101. In the preferred embodiment, the sleeve is fabricated of a quartz with a $125\mu$ wall thickness. In an alternative embodiment, the sleeve 101 is formed of a Pyrex capillary which has a wall thickness of $500-700\mu$. Variations are, of course, possible. Typically, the sleeve 101 includes an axial bore 102 therethrough. The axial bore has a diameter of approximately $260\mu$. A separation (or input) column 103 is inserted within the bore 102 of the sleeve 101. The separation column 103 is, typically, fabricated of Pyrex or quartz and has an internal axial bore 104 having a diameter of approximately $75\mu$. An optional exit column 105 is shown at the output end of the detector assembly 100. The exit column 105 is substantially similar to the separation column 103 and includes an axial bore 106 which is, typically, of the same internal diameter as the separation column 103.

However, it should be noted that the exit column 105 is not required in all applications. Typically, exit column 105 is utilized to enhance the fluid flow through the detector assembly 100, in particular, past the optical detection station, as described hereinafter. In the event that fluid flow through the separation column 103 and past the detection station is appropriate to maintain integrity of the flow and of the specimen through the detection station, the exit column 105 can be omitted.

In the detection station, there is shown an input fiber optic conductor 107. The conductor 107 is conventional and includes a fiber optic core 108 of typical fiber optic conductors on the order of $50\mu$. The fiber optic core 108 is encased in a conventional cladding 109 which has an outer diameter of $70\mu$. An outer jacket 110 is provided over and around the cladding 109 and has an outer diameter of approximately $125\mu$. These dimensions are, of course, representative only.

An output fiber optic conductor 111 comprises a conventional fiber optic core 112 having a diameter of approximately $100\mu$ covered by cladding 113 and jacket 114. The cladding 113 and jacket 114 have outside diameters of approximately $120\mu$ and $140\mu$, respectively. The output fiber optic core 112 is, preferably, larger than the input fiber optic core 108 by at least the diametrical increase in the light spot size due to the angle of the numerical aperture and the spreading of the rays across the path between the fiber faces.

The fiber optic conductors 107 and 111 pass through precisely dimensional bores 120 and 121, respectively, which pass through the sides of the support sleeve 101. These apertures or bores 120, 121 can be drilled or otherwise provided in keeping with the precision techniques available.

The input fiber optic conductor 107 is adhered to the support sleeve 101 by means of a suitable adhesive bead 115. Likewise, the output fiber optic conductor 111 is adhered to the support sleeve 101 by an adhesive bead 116. The adhesive beads 115 and 116 can be any suitable adhesive such as glue, epoxy or the like which will adhere to both the fiber optic conductor jackets 110, 114 and the outer surface of the support sleeve 101.

In conjunction with the detector assembly 100 shown in FIG. 1, an input unit 190 and an output unit 191 are connected to opposite ends of the support sleeve 101 and the columns 103, 105 included therein. The input and output units 190, 191 are conventional in the capillary electrophoresis art and are used to supply and receive the sample which is to be passed through the detector assembly 100 and evaluated.

A source 180 and a detector 181 are connected to the external ends of the input fiber optic conductor 107 and the output fiber optic conductor 111, respectively. The source 180 can be any suitable optical source such as a laser, ultraviolet light or the like, as dictated by the type of detection process involved. The precise angle of light entering the source 180 end of the input fiber optic conductor 107 is not critical, provided that the light essentially fills or falls within the numerical aperture of the input fiber optic conductor 107. The detector 181 can be any suitable light detector which can be connected to a suitable recording apparatus, if so desired.

The detector assembly 100 described above creates a detection station 150 which is defined to be disposed between the internal ends of the input and output fiber optic conductors 107 and 111, per se, and at the internal end of the separation column 103. Thus, as the specimen passes through the bore 104 in separation column 103, it is acted upon and separated in accordance with conventional techniques. The separated specimen then passes out of the internal end of the separation column 103, through the detection station 150 and out the exit column 105, if provided as is determined by the process involved.

The internal ends of the separation column 103 and exit column 105 (if provided) are, typically, in abutment with the outer surface of the respective fiber optic conductors 107 or 111 (or at least the larger diameter one thereof). However, this spacing is not absolutely critical in most instances. That is, in most cases it has been found that the hydrodynamic forces on the fluid specimens are sufficient to cause the specimen to pass through the detection station 150 with sufficient integrity to provide an accurate reading by the system.

It is also noted that the end of each fiber optic conductor 107, 111 is coincident with the diameter of the end of the bore 104 in the separation column 103 (and bore 106 in the exit column 105 where provided). This dimension is assured during the assembly process by using a properly dimensioned spacer (as is described below) in the system when the fiber optic conductors 107, 111 are installed through the bores 120, 121 in the support sleeve 101. Thus, the light rays pass directly from the input fiber optic conductor 107 into (and therethrough) the fluid specimens in the detection station 150. Similarly, light rays pass directly from (through) the specimen to the output fiber optic conductor 111. This arrangement substantially reduces any refraction, diffraction or any of the optical shortcomings evident in prior art devices which cause the light rays to pass through multilayers of glass, quartz, Pyrex or other material. Moreover, the interface between the fiber optic conductors 107, 111 and the specimen is not quite so complicated as the prior art cylindrical interfaces. Thus, improved sampling techniques are permitted.

Referring now to FIG. 2, thee is shown a cross-sectional view of the detector assembly 100 taken along the lines 2—2 in FIG. 1. For convenience, the input 190, output 191, source 180 and detector 181 components have been omitted.

Thus, as shown in FIG. 2, the fiber optic conductors 107 and 111 pass through bores 120 and 121, respectively, which extend through the support sleeve 101. These bores 120 and 121 can be drilled or otherwise provided. The internal ends of the fiber optic conductors 107 and 111 are aligned with the inside surface of bore 104 in separation column 103. The adhesive beads 115 and 116 retain the fiber optic conductors 107 and 111 to the support sleeve 101.

Referring concurrently to FIGS. 1 and 2, the method of fabricating the detector assembly 100 is further described.

Initially, the support sleeve 101 is provided with the proper dimensions, primarily of inner and outer diameters. The bores 120 and 121 are formed in and through the outer walls of the support sleeve 101. The bores 120 and 121 are formed by means of laser drilling, ion etching, or any other suitable process which will produce accurately aligned, properly dimensioned bores in the material of the support sleeve. The bores 120 and 121 are diametrically opposed relative to the support sleeve 101 and are of the appropriate dimensions to snugly receive the fiber optic conductors 107 and 111, respectively.

Initially, a thin, relatively stiff alignment wire 175 of the proper outer diameter to snugly (but slidably) fit within the bore 104 of separation column 103 is inserted into bore 104. The wire 175 is then threaded or slipped through the axial bore 102 in the support sleeve 101. In the event that an exit column 105 is to be utilized, it is threaded to slipped onto the other end of the wire 175 which has passed through the support sleeve 101. The separation and exit columns 103 and 105 are then slipped along the wire 175 into the support sleeve 101. However, a space remains between the internal ends of the respective columns 103, 105 adjacent the detection station 150. At that juncture, the conductors 107 and 111 are inserted into and through the bores 120 and 121, respectively. The conductors 107 and 111 are then slid through the support sleeve 101 until contact is made with the wire 175 (see FIG. 2). When both of the fiber optic conductors 107, 111 are in abutment with the wire 175, the spacing therebetween is determined to be optimal. At that juncture, the adhesive beads 115 and 116 are put in place to secure the fiber optic conductors 107 and 111 to the support sleeve 101. Thereafter, the columns 103 and 105 can be slipped further along the wire 175 until brought into abutment with the fiber optic conductors 107 and/or 111. At this point, the columns 103, 105 are caused to adhere to the support sleeve 101 with adhesive bonding material similar to the material adhering the optical fibers to the sleeve 101. The wire 175 is then removed from the assembly 100. The wire 175 has, thus, permitted the ends of the fiber optic conductors 107 and 111 to be properly aligned with (and substantially coextensive with) the internal bores 104 and 106 to provide adequate and precise flow paths for the specimen to be detected.

In the idealized situation, the fiber optic conductors 107 and 111 will transmit the optical beam with a large degree of integrity within the numerical aperture (N.A.). However, the light will diverge as it traverses the gap between the end of the fibers. Thus, it is desirable to provide the fiber optic core 112 of the output conductor 111 with a slightly larger diameter than the fiber optic core 108 of the input conductor 107, as noted above and shown in the drawings.

Referring now to FIG. 3, there is shown an enlarged, cross-sectional view of the detection station 150 of the apparatus. It is seen that certain light rays have angles of reflection (or the like) which permit these rays to escape from the core 108 of the input fiber optic conductor 107. For example, ray 360 is able to escape from optical fiber 107. This is of little consequence because of the cladding 109 which surrounds the fiber optic core 108.

Other rays, such as ray 361, are retained in the fiber optic core 108 and pass out of the free end thereof. This emitted light defines a conical angle referred to as the numerical aperture (N.A.). The definition of N.A., as is well known in the art, is sin $\theta$, where $\theta$ is the angle between the axis of the fiber and the envelope of light emitted. Thus, by making output fiber optic core 112 larger in diameter than input fiber optic core 108, the entire light envelope can be received at the output. Conversely, by placing the internal ends of the input and output fiber optic conductors 107 and 111 as close together as possible, spread of light defined by the N.A. and the effects of stray light are reduced. Moreover, by placing the internal ends of the fiber optic conductors 107 and 111 in the fluid path, the stray light, scattered light, refraction and reflection (and other optical phenomenon) are reduced. Thus, improved analysis can be achieved with this apparatus.

Moreover, it is highly desirable to adapt the carrier buffer for the specimen to be detected to have a refractive index which is as close to the refractive index of the fiber optic core 108 and 112 as possible in order to prevent refraction and diffraction of the light signal at the boundaries between the media through which the optical signal passes.

In the present invention, the output end of fiber optic conductor 107 is immersed in the fluid path. This arrangement is advantageous in that the interrogating rays directly enter the solution to be measured, thereby eliminating stray paths. In addition, scatter (which is a source of stray light) that occurs at a surface is a function of the difference in refractive index between the two materials at the surface. The solutions in the bore of the capillary are aqueous which places the refractive index at or near 1.333. The fiber optic material is silica with a refractive index at 1.46. Conversely, if the fibers are not immersed in the solution, the difference is between 1.09 for air and 1.46 for the fiber.

In the summary, this arrangement affords advantages of control of the optical path length, avoidance of stray light and reduction of interface scatter.

Thus, there is shown and described a unique design and concept of capillary electrophoresis detection. The particular configuration shown and described herein relates to precision detector assemblies using optical detection. While this description is directed to a particular embodiment, it is understood that those skilled in the art may conceive modifications and/or variations to the specific embodiments shown and described herein. It is understood that the description herein is intended to be illustrative only and is not intended to be limitative. Rather, the scope of the invention described herein is limited only by the claims appended hereto.

I claim:

1. A capillary electrophoresis detector comprising:
   capillary means for providing a capillary flow path for a sample;
   light means for defining an optical path and including light transmitting members; and
   sleeve means for supporting said capillary means and positioning said light transmitting members on opposite sides of said sleeve means with respect to said capillary flow such that said optical path is across said capillary flow, wherein said light transmitting members extend into an inner space within said sleeve means.

2. A capillary electrophoresis detector comprising:
   capillary means for providing a capillary flow path for a sample, said capillary means including an axial bore therein;
   light means for defining an optical path and including light transmitting members; said light transmitting members terminating at the bore within said capillary means; and
   sleeve means for supporting said capillary means and positioning said light transmitting members on opposite sides of said sleeve means with respect to said capillary flow such that said optical path is across said capillary flow.

3. A capillary electrophoresis detector comprising:
   capillary means for providing a capillary flow path for a sample;
   light means for defining an optical path and including light transmitting members; said light means including a pair of aligned fiber optic conductors, a first one of said pair of fiber optic conductors being smaller in diameter than the second one of said pair of fiber optic conductors; and
   sleeve means for supporting said capillary means and positioning said light transmitting members on opposite sides of said sleeve means with respect to said capillary flow such that said optical path is across said capillary flow.

4. The detector recited in claim 3 wherein, said sleeve means is a hollow tube.

5. The detector recited in claim 4 wherein, said capillary means is supported within said sleeve means.

6. The detector recited in claim 3 wherein, said capillary means includes at least one section disposed above said light means.

7. The detector recited in claim 3 wherein, said capillary means includes at least two sections disposed on opposite sides of said light means.

8. The detector recited in claim 3 wherein,
   said light means includes a light source connected to said first one of said pair of fiber optic conductors.

9. The detector recited in claim 8 wherein,
   said light means includes a light receiver connected to said second one of said pair of fiber optic conductors.

10. The detector recited in claim 8 wherein, said light source comprises a laser means.

11. The detector recited in claim 3 wherein, said sleeve means is fabricated of quartz.

12. A capillary electrophoresis detector comprising:
    capillary means for providing a capillary flow path for a sample;
    light means for defining an optical path;
    sleeve means for supporting said capillary means and positioning said light means with respect to said capillary flow such that said optical path is across said capillary flow; and
    said light means exhibits a refractive index which is substantially similar to the refractive index of the sample.

13. A capillary electrophoresis detector comprising:
    a first capillary column having an end;
    a second capillary column having an end;
    an input optical fiber having an end;
    an output optical fiber having an end; and
    a support sleeve, the support sleeve including opposing radial bores receiving and retaining the input and output optical fibers with the ends of the input and output optical fibers fixed at a distance substantially equal to the inside diameter of at least one of the first or second capillary columns, the support sleeve coaxially retaining and supporting the first and second capillary columns such that ends of such columns abut at least one of the input or output optical fibers.

14. A capillary electrophoresis detector comprising:
    capillary means for providing an axial bore for a capillary flow path for a sample;
    a support sleeve with a pair of diametrically opposed holes therethrough over at least a portion of said capillary;
    a pair of radiation transmitting members in said pair of holes in said support sleeve; and at least one of the radiation members terminating at the bore within the capillary means.

15. A detector as claimed in claim 14 wherein both radiation members terminate at the bore.

16. A capillary electrophoresis detector fabricated by the process of:
    placing at least a portion of an elongated member into the bore in a capillary,
    placing a support sleeve with a pair of diametrically opposed holes therethrough over at least a portion of said capillary and said elongated member,
    inserting a pair of radiation transmitting members into said pair of holes in said support sleeve into abutment with said elongated member, adhering said radiation transmitting members to said support sleeve, and removing said elongated member from said capillary.

* * * * *